United States Patent
Campbell et al.

[11] Patent Number: 5,456,666
[45] Date of Patent: Oct. 10, 1995

[54] MEDICAL BALLOON FOLDING INTO PREDETERMINED SHAPES AND METHOD

[75] Inventors: Andrew J. Campbell, Reading; Ralph J. Barry, Jr., Hudson, both of Mass.

[73] Assignee: Boston Scientific Corp, Natick, Mass.

[21] Appl. No.: 233,391

[22] Filed: Apr. 26, 1994

[51] Int. Cl.$^6$ .................................................. A61M 29/00
[52] U.S. Cl. ............................................... 604/96; 606/194
[58] Field of Search ........................... 604/96, 101, 102, 604/103; 606/191–194

[56] References Cited

U.S. PATENT DOCUMENTS

| | | |
|---|---|---|
| 2,330,399 | 9/1943 | Winder . |
| 4,276,874 | 7/1981 | Wolvek et al. . |
| 4,743,258 | 5/1988 | Ikada et al. . |
| 4,820,349 | 4/1989 | Saab . |
| 4,906,244 | 3/1990 | Pinchuk et al. . |
| 4,938,676 | 7/1990 | Jackowski et al. . |
| 4,941,877 | 1/1990 | Montano . |
| 5,015,230 | 5/1991 | Martin et al. . |
| 5,015,231 | 5/1991 | Kieth et al. . |
| 5,017,325 | 5/1991 | Jackowski et al. . |
| 5,037,392 | 8/1991 | Hillstead . |
| 5,147,302 | 9/1992 | Eutenuer et al. . |
| 5,250,070 | 10/1993 | Parodi . |
| 5,342,307 | 8/1994 | Euteneuer et al. ................. 604/96 X |

Primary Examiner—John D. Yasko

[57] ABSTRACT

An inflatable medical balloon (40) at its distal end for introduction into a body part especially through an endoscope (46) and method of making the balloon. When fully inflated, the balloon (40) is a continuous body of balloon material (which may be formed of one or more polymeric layers) with a generally cylindrical shape and four ribs (44) formed in the body. The ribs (44) are longitudinally and equidistantly arranged around an axis (A) which extends from the proximal end to the distal end of the balloon (40). The ribs (44) are formed of stressed balloon material. Webs (45) of less stressed balloon material are disposed between the ribs (44), the ribs and the webs forming the balloon (40) and being expandable from a folded condition for insertion into the body part to an expanded condition with a generally cylindrical shape and a diameter substantially greater than the folded condition whereby to provide medical treatment and, after treatment, being revertible into a folded condition of predetermined configuration with the webs (45) between the ribs (44) collapsing inwardly towards the axis (A). The balloon with its ribs is made by placing an untensioned balloon in a mold (15) having a square cross section with pyramidal end members (3). The mold is heated and balloon is inflated to form ribs (44) of stressed balloon material with webs (45) of less stressed material between them.

20 Claims, 2 Drawing Sheets

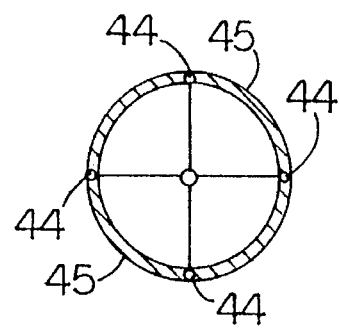
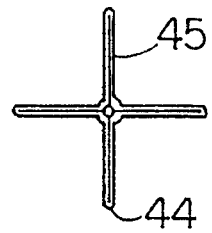
FIG. 4  FIG. 5
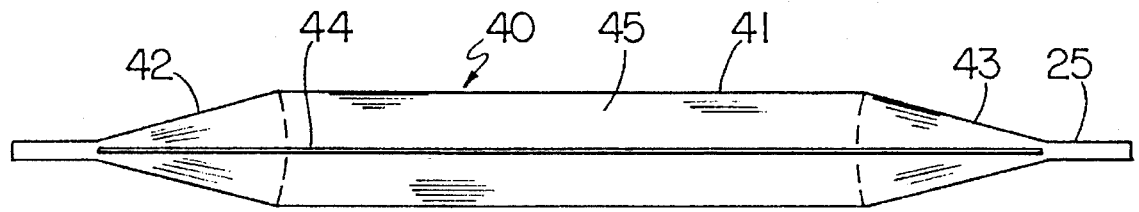
FIG. 6
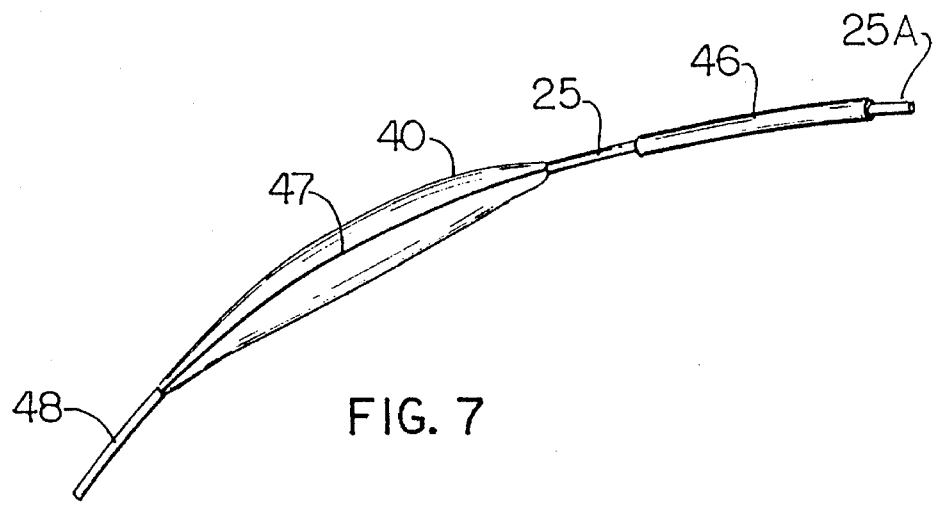
FIG. 7

MEDICAL BALLOON FOLDING INTO PREDETERMINED SHAPES AND METHOD

The present invention relates to balloons for catheters for insertion into parts of the body and particularly to a catheter with a balloon that after expansion, use and evacuation of inflation fluids will fold itself into a predetermined shape of limited diameter so that it can be easily withdrawn from the body. The balloon of the present invention has special use with an endotracheal tube in which a folded balloon catheter is forced into the endotracheal tube before insertion into the trachea and before inflation. After performing a medical procedure, the balloon is deflated and must be withdrawn back through the tube. Inflation of the balloon, we have found, causes the diameter of the balloon to increase from its original folded and wrapped size to one which is large and bulky after deflation. The bulky deflated balloon is the quite difficult to withdraw through the tube.

DESCRIPTION OF THE PRIOR ART

In the prior art, catheters with single-walled balloons which collapse onto themselves are known. Exemplary of such a balloon is the device disclosed in the Hillstead, U.S. Pat. No. 5,037,392, in which a dilation balloon assembly is disclosed with three axially-extending longitudinal creases. Hillstead found when balloons were deflated after use, the lateral cross-section of the balloon could be greater than the diameter or lateral extent of a fully inflated or partially inflated balloon due to flattening. Hillstead's balloon uses three side walls to eliminate flattening upon deflation into a wing-like configuration. The balloon was particularly designed to insert a stent within an artery and to enable the balloon to expand the stent to a full size to engage the walls of the artery. The three-sided balloon can have relatively sharp sides due to the an angle of about 120°. Triangular cross-sections are blade-like and can traumatically engage the walls of the vessel in which it is inserted.

The Schultze, U.S. Pat. No. 4,141,364, discloses an endotracheal tube which is collapsed transversely to the longitudinal dimension of the tube for insertion into the trachea of the patient. After the tube is in place it is expanded to open an unobstructed passageway therethrough by means of an expandable cuff provided on the exterior of the tube to afford a seal between the trachea and the tube.

The Vigil, U.S. Pat. No. 3,209,799, discloses a angioplasty device in which four atherotomes are attached to the exterior of a balloon and the balloon is treated so that the atherotomes will be enshrouded in the balloon when it is deflated to provide covers which protect the patient from contact with the atherotomes' blades.

The Smith, U.S. Pat. No. 5,087,246, discloses a medical balloon that forms into flutes upon deflation to enable the balloon to be easily withdrawn through the endoscope. The flutes are formed by tensioning (stretching) then heating the tensioned balloon. We have found that tensioning weakens the catheter assembly at the balloon walls and can cause premature product failure.

The Farr et al., U.S. Pat. No. 5,226,887, discloses a medical balloon that, when the balloon is neither inflated nor collapsed, has folding regions that are flat and reinforcing regions that are curved. The folding regions are less stiff than the reinforcing regions. The reinforcing regions, however, do not extend the full length of the balloon but rather are radially off-set at the distal ends which places stresses on the balloon and makes it difficult to predictably fold the balloon after use and easily withdraw it through an endoscope.

SUMMARY OF THE INVENTION

According to the present invention we have developed a balloon catheter for insertion into a body part, for example the trachea, by means of an endotracheal tube. The inner diameter of the tube is only slightly greater than the outer diameter of the folded and wrapped balloon. The balloon is made of balloon material which can be expanded to a generally cylindrical shape. Four ribs are formed in the balloon material and these ribs are longitudinally arranged and equidistantly separated from each other about the axis of the balloon. They extend from the proximal to the distal end of the balloon. Stiff ribs are formed of stressed balloon material and less stiff webs between the ribs are formed of less stressed material. The balloon is expandable from a folded and wrapped configuration before use to an expanded condition with a generally cylindrical shape to provide the medical treatment. After the medical procedure, the balloon is deflated (by evacuation of the inflation fluid) to a diameter which allows it to be narrow enough to reenter the tube through which it was originally inserted.

One aspect of the invention involves a balloon for a catheter for introduction into a body part through an endoscope. The catheter includes a hollow shaft with a proximal and a distal end. The balloon is formed of a continuous body of untensioned balloon material and has a generally cylindrical shape. Four ribs are disposed in the balloon and are formed of stressed balloon material. The ribs are longitudinally and equidistantly arranged around an axis and extend as straight lines over the distance between the proximal and distal end of the balloon. Webs of less stressed balloon material disposed between the ribs. The ribs and the webs form the balloon and are expandable from the folded condition of predetermined shape to the expanded condition with a generally cylindrical shape and a diameter substantially greater than the folded condition. The introduction of inflation fluid through the proximal end of the shaft inflates the balloon so the medical treatment can be provided. After treatment, the balloon is revertible to the folded condition of predetermined shape with the webs between the ribs collapsing inwardly from the proximal to the distal end of the balloon towards the axis by withdrawal of the inflation fluid (without the use of tension) so the balloon can be withdrawn through the endoscope. A closure tip is disposed at the distal end of the balloon and a loosely floating guide wire is disposed within the balloon and in the tip. The guide wire extends from the shaft to the closure and engages both the shaft and the closure.

Another aspect of the invention involves a method of forming a medical balloon for attachment to a hollow catheter shaft and for subsequent introduction into a body part. The balloon is deflatable into a predetermined shape of minimal dimensions to be withdrawn through a tube of a diameter substantially the same as the minimum dimension of the balloon. According to the method we place into a mold a preformed medical balloon formed of a continuous body of balloon material that has a generally cylindrical shape when inflated. The mold has a length corresponding to the desired length of the balloon and a generally polygonal cross section with side walls of substantially the same width connected by corners, the spacing between opposed corners approximating the desired diameter of the balloon when inflated. The mold further has end members at each end and each of the end members has a pyramidal shape terminating in an apex. The corners of the mold correspond with the corners of the end members and openings are formed at the apexes for clamps that hold the balloon in place within the mold and allow for the introduction of inflation fluid. The mold is heated to the softening point of the balloon and a pressurizing fluid is forced into the balloon to urge the balloon material against the sidewalls, into the corners and the end members whereby to establish stressed areas where the balloon engages the corners and form four radially arranged ribs with webs therebetween. Temperatures used are between about 160° and 195° C. and pressures are between about 140 and 200 psi. The ribs extend continuously from the distal to the proximal ends of the balloon. The webs are less stressed than the ribs due to greater expansion distances of the balloon material into the corners than to the sidewalls of the mold. The ribs and the webs form the balloon and are expandable from a folded condition for insertion into the body part to an expanded condition with a diameter substantially greater than its folded condition whereby to provide medical treatment to the part and thence, after treatment, into a folded condition with the webs collapsing inwardly towards the axis, the ribs extending parallel to the axis, each of the ribs being radially offset from adjacent ribs by substantially the same distance, whereby to form a balloon with ribs and webs as the body of the balloon. The balloon is expandable to a generally cylindrical shape by the introduction of an expansion fluid and then collapsible upon the withdrawal of the fluid into a structure wherein the webs collapse between the ribs towards the axis to enable easy withdrawal from the body part.

In the preferred embodiment we use conventional balloon-forming stock of polyethylene terephthalate (PET). Usually the PET is disposed between co-extruded layers of Selar such as disclosed in the Wang et al U.S. Pat. No. 5,195,969 and incorporated herein by reference. Selar is a barrier resin made by the DuPont de ne Mours Company of Wilmington, Del. The balloon of our invention can be made by placing a pre-blown partially inflated balloon having a conventional wall thickness in a mold having a length corresponding to the desired length of the balloon and a generally square cross-section with four side walls of substantially the same width connected by four corners. The sidewalls of the mold have widths between about 0.002 and 0.6 in. and each are of substantially the same, thereby providing a mold with a generally square cross section and corners of 90 degrees. Each of the end members of the mold have a pyramidal shape with the base corresponding to the end of the polygonal section of the mold. The mold is heated to the softening point of the plastic balloon material placed therein, generally between about 160° and 195° C., and a pressurizing fluid, eg. nitrogen, is forced into the balloon so that the balloon expands to urge against the side walls, into the corners and against the end members. When the balloon expands into the corners, the expansion of the balloon is greater for the ribs than for the webs therebetween since the distance between the axis and the corners is greater than the distance between the axis and the side walls. This additional stretching puts greater stress on the balloon where it meets the corners then where it meets the side walls of the mold. The additional stress makes the ribs more rigid than the webs which are therebetween. The balloon is then removed from the mold. It is expandable to the generally cylindrical shape by the introduction of expansion fluid and thence collapsible upon withdrawal of the fluid into a structure where the webs between the rips collapse towards the axis to enable the balloon to be easily drawn through the tube of substantially the same inner diameter as the outer diameter of the original wrapped and folded balloon.

BRIEF DESCRIPTION OF THE DRAWINGS

FIGS. 3, 4 and 5 are cross-sectional views of the balloon of the present invention in three stages of inflation: partial, full and evacuated.

FIG. 6 is a side elevational view of the expanded balloon according to our invention.

FIG. 7 is a side view of a deflated balloon extending from an endotracheal tube.

DESCRIPTION OF THE PREFERRED EMBODIMENTS

Figure 1:
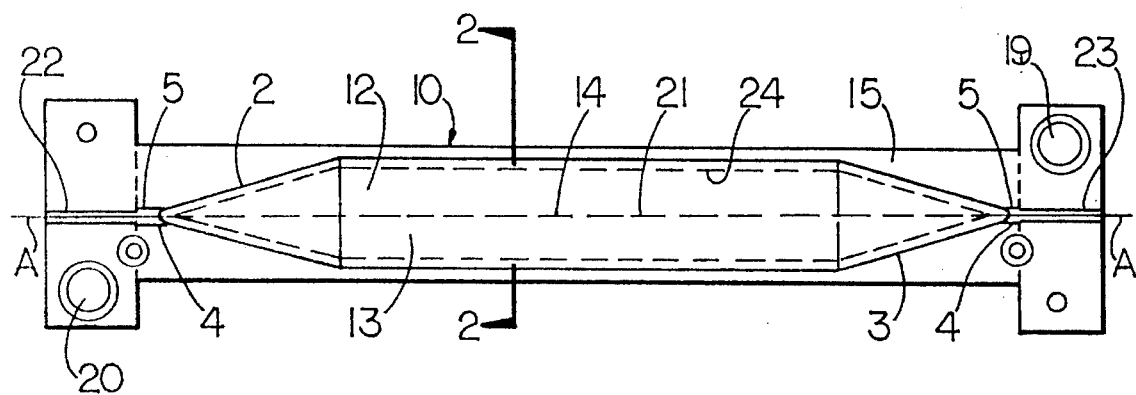
FIG. 1 is a plan view of one half of a mold showing the open cavity which receives the balloon.
Figure 2:
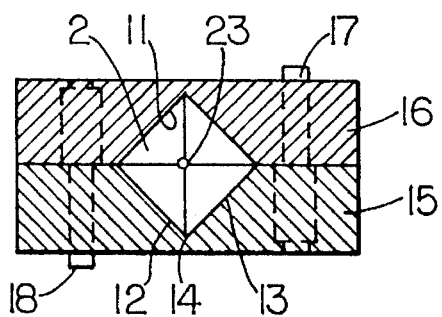
FIG. 2 is a cross-sectional view of the top and bottom of the mold shown in FIG. 1.

Referring now to FIG. 1 one half of a mold for forming the balloon of the present invention is shown and in FIG. 2 both halves are shown. The mold body 10 includes a cavity 11 with side walls 12 and 13. A corner 14 is disposed between the side walls. Each of the side walls 12 and 13 have substantially the same dimensions. The corner 14 is a 90° angle. At each end of the sidewalls 12 and 13 are pyramidal-shaped end members 2 and 3. The side walls of the body of the mold and the base of each of the end members 2 and 3 have the same dimensions so as to provide continuous corners that terminate in an apex. A hole is formed at the apexes at each end of the end members 2 and 3 to receive the ends of the balloon.

FIG. 1 shows the lower half 15 of the mold as seen in FIG. 2. An upper half 16 cooperates with the lower half 15 to form a cavity with four corners and four side walls. The upper half 16 and the lower half 15 are bolted together by bolts 17 and 18 that fit in holes 19 and 20.

An axis A passes from a left holder slot 22 through a right holder slot 23. These holder slots are of a diameter to hold a balloon 24 (shown in dotted lines). A gas is blown into the balloon 24, one end of which is blocked off, to expand it. The mold 10 is heated in conventional ways to soften the plastic of the balloon 24 and form the ribs and the webs therebetween as will be described hereinafter. The balloon is not tensioned prior to disposition in the mold, thereby not stressing the balloon prior to its expansion.

A view of a fully expanded balloon 40 is shown in FIG. 6. When fully expanded it has a generally cylindrical shape in its body section 41. End walls 42 and 43, in inflated condition, have generally frustroconical shapes although, they too, have the ribs mentioned above. The balloon 40 is formed of conventional medical balloon forming materials such as polyethylene terephthalate (PET). In the preferred embodiment of the present invention we use a coaxial extrusion of PET with Selar on each side thereof and thicknesses of Selar between about 0.0001 and 0.00005 in. in each layer.

Figure 3:
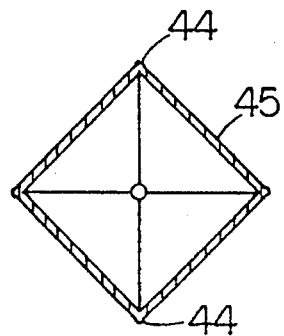

Webs 45, as better shown in FIGS. 3, 4 and 5, are disposed between ribs 44. The balloon has three configurations. In the expanded state, as shown in FIGS. 4 and 6, it has a generally cylindrical shape. Prior to the expansion it is folded and wrapped, generally upon itself so that it can be readily inflated. Folding and wrapping is conventional in the medical balloon art to reduce the size of the balloon as much as possible. As the balloon is inflated by blowing inflation fluid into tube 25 that is conventionally attached to the proximal end of the balloon 24. It reaches an intermediate stage, as shown in FIG. 3, in which it has a generally square cross-section. This intermediate stage is passed during the inflation until the balloon reaches the cylindrical shape shown in FIG. 4. The medical procedure is performed while it is in the cylindrical shape and while it is at its maximum diameter.

Following inflation and use, the inflating media is withdrawn through tube 25 and the four ribs 44 and the four webs 45 collapse inwardly towards the axis of the balloon. As shown in FIG. 5 the ribs 44 are relatively stiff and support the webs 45 disposed therebetween. Thus the webs 45 collapse more readily. A smaller profile is presented which enables the balloon to be easily drawn into the endotracheal tube that was used for insertion of the balloon into the body. Comparing a balloon made in an octagonally cross sectioned mold with one made according to the present invention, that is a mold with a square cross section, we found that it took 6.65 lbs. to withdraw an octagonally shaped 18 mm. balloon from an endoscope whereas it only took a mean force of 5.0 lbs. to withdraw the square shaped balloon from an endoscope of the same size. Thus the impact of the use of a square mold was to decrease the force required to withdraw the balloon from the endoscope. With balloons without ribs the balloon collapsed into a pancake-like structure which was extremely difficult to withdraw through the endoscope.

Referring to FIG. 7 the balloon 40 is shown with the inflation media withdrawn through tube 25. A conventional stiffening wire 47 is disposed within the balloon 40 and extends from a closed distal end 48 through the balloon and into the tube 25 and out its end. Because of the relative stiffness between the webs and the ribs as described above withdrawal of the inflation media will cause the webs to collapse inwardly between the ribs. Pulling the end 25A of the tube will cause the balloon 40 to be easily drawn into an endotracheal tube 46 with a minimum of difficulty so the balloon 40 can be easily removed from the body.

With the four sided balloon of the present invention we found that it was possible to inflate and deflate the balloon many times (e.g. 40 cycles at operating pressures) and obtain the same folding action repeatably with the webs collapsing toward the axis and being supported by the ribs. When withdrawn through the tube, the ribs are squeezed towards the axis of the balloon and the webs fold generally in the middle of the spaces between them thereby presenting a profile that approximates the originally folded and wrapped balloon to enable it to be easily withdrawn through the tube. Moreover the 90° angles provided by the use of four sides is substantially "rounded" and there are no "sharp" edges which might serve to impede catheter withdrawal or in the worst case abrade tissue. In addition the continuous ribs, extending from the distal to the proximal end of the balloon as a straight line enable the entire balloon to be uniformly collapsed around its axis thereby enhancing the strength of the balloon.

The balloon preform is loaded into a balloon machine and then blown with nitrogen in a heated oil bath using cones on either side of the unit to control the size, as is conventional. The outside diameter of the balloon is 80 to 90% of its net shape. The balloon is then removed from the machine and cleaned of any residual oil. The final dimensions of the balloon are then established in a heat set process. In this process the cylindrical balloon is placed into a mold with a square cross-section. The area of the cavity perimeter is 4.275% greater than the final balloon target circumference. The balloon is lowered into the lower half of an aluminum mold and inflated to 10 psi. The top half of the mold is then clamped onto the lower half to cover the balloon. The balloon is then inflated in two or more stages to a pressure between about 140 to 200 psi while the mold is heated to 160° to 195° C. During this process the balloon is stretched in an axial direction the combination axial and radial stretching encourages additional biaxial orientation.

It is apparent that modifications and changes can be made within the spirit and scope of the present invention. It is our intention, however, only to be limited by the scope of the appended claims.

As our invention we claim:

1. A balloon catheter for introduction into a body part through an endoscope, said catheter having a shaft with a proximal and a distal end, said shaft further having at least one lumen and a balloon attached to the distal end of said shaft, said balloon having a proximal and a distal end, said catheter comprising:

a balloon formed of a continuous body of untensioned balloon material and having a generally cylindrical shape;

four ribs disposed in said balloon and being formed of stressed balloon material, said ribs being longitudinally and equidistantly arranged around an axis, said ribs extending as straight lines over the distance between said proximal and distal end of said balloon;

webs of less stressed balloon material disposed between said ribs, said ribs and said webs forming said balloon and being expandable from a folded condition of a predetermined shape for insertion into said body part through said endoscope to an expanded condition with a generally cylindrical shape and a diameter substantially greater than said folded condition by the introduction of inflation fluid through the proximal end of said shaft whereby to provide medical treatment to said part and, after treatment, being revertible into a folded condition with the webs between said ribs collapsing inwardly from the proximal to the distal end of said balloon towards said axis by withdrawal of the inflation fluid without the use of tension to enable said balloon to be withdrawn through said endoscope;

means forming a closure disposed at the distal end of said balloon;

a stiffening wire to stiffen said balloon, said wire extending from said shaft to said closure means and engaging both said shaft and said closure means.

2. The catheter according to claim 1 wherein the stiffening wire is attached to the proximal end of said shaft and the distal end of said balloon.

3. The catheter according to claim 1 wherein the balloon is formed of polyethylene terephthalate.

4. The catheter according to claim 1 wherein the balloon is formed of a base layer of polyethylene terephthalate with a layer of Selar disposed on either side of said base layer.

5. A balloon catheter for introduction into a tubular body conduit, said catheter having a shaft with a proximal and a distal end, said shaft further having at least one lumen and a balloon attached to the distal end of said shaft, said balloon having a proximal and a distal end, said catheter comprising:

a balloon formed of a continuous body of untensioned balloon material and having a generally cylindrical shape;

four ribs disposed in said balloon and being formed of stressed balloon material, said ribs being longitudinally and equidistantly arranged around an axis, said ribs extending as straight lines over the distance between said proximal and distal end of said balloon;

webs of less stressed balloon material disposed between said ribs, said ribs and said webs forming said balloon and being expandable from a folded condition of a predetermined shape for insertion into said body conduit to an expanded condition with a generally cylindrical shape and a diameter substantially greater than said folded condition by the introduction of inflation fluid through the proximal end of said shaft whereby to provide medical treatment within said conduit and, after treatment, being revertible into a folded condition with the webs between said ribs collapsing inwardly from the proximal to the distal end of said balloon towards said axis by withdrawal of the inflation fluid without the use of tension to enable said balloon to be withdrawn from said conduit;

means forming a closure disposed at the distal end of said balloon;

a stiffening wire to stiffen said balloon, said wire extending from said shaft to said closure means and engaging both said shaft and said closure means.

6. The catheter according to claim 5 wherein the stiffening wire is attached to the proximal end of said shaft and the distal end of said balloon.

7. The catheter according to claim 5 wherein the balloon is formed of polyethylene terephthalate.

8. The catheter according to claim 5 wherein the balloon is formed of a base layer of polyethylene terephthalate with a layer of Selar disposed on either side of said base layer.

9. A medical balloon for subsequent attachment to a catheter shaft having a lumen for the introduction of an inflation fluid and subsequent introduction into a body conduit, said balloon being deflatable into a predetermined shape of minimal dimensions, said balloon being formed by the steps comprising:

placing into an elongated mold an untensioned, preformed medical balloon, said balloon having continuous body of balloon material terminating in a tip and having a generally cylindrical shape when inflated, said mold having a length corresponding to the desired length of said balloon and a generally polygonal cross section with side walls of substantially the same width, said side walls being connected by corners, the spacing between opposed corners approximating the desired diameter of the balloon when inflated, said mold further having end members at each end, each of said end members having a pyramidal shape terminating in an apex, said corners of said mold corresponding with the corners of the end members and openings at the apexes to receive the catheter shaft and the tip of the balloon;

heating said mold to the softening point of the balloon and forcing a pressurizing fluid into said balloon to urge said balloon material against the sidewalls and into said corners and into said end members whereby to establish stressed areas where said balloon engages said corners to form four radially arranged ribs with webs disposed therebetween, said ribs extending continuously from the distal to the proximal ends of said balloon, said webs being less stressed than said ribs due to greater expansion distances of said balloon material into said corners than to said sidewalls of said mold, said ribs and said webs forming said balloon and being expandable from a folded condition for insertion into said body conduit to an expanded condition with a diameter substantially greater than its folded condition whereby to provide medical treatment to said conduit and thence, after treatment, into a folded condition with the webs collapsing inwardly towards said axis, said ribs extending parallel to said axis, each of said ribs being radially offset from adjacent ribs by substantially the same distance, whereby to form a balloon with ribs and webs as the body of the balloon, said balloon being expandable to a generally cylindrical shape by the introduction of an expansion fluid and then collapsible upon the withdrawal of said fluid into a structure wherein said webs collapse between said ribs towards said axis to enable easy withdrawal from said body conduit;

opening said mold and removing said balloon from said mold.

10. The balloon according to claim 9 wherein the balloon is heated in the mold to a temperature between about 160° and 195° C. and inflated at pressures between about 140 and 200 psi.

11. The balloon according to claim 9 wherein the balloon is formed of polyethylene terephthalate.

12. The balloon according to claim 9 wherein the balloon is formed of a base layer of polyethylene terephthalate with a layer of Selar polymer disposed on at least one side of said base layer.

13. An inflatable medical balloon for introduction into a body conduit, said balloon being deflatable into a predetermined shape of minimal dimensions, said balloon being formed by the steps comprising:

placing an untensioned, preformed medical balloon having continuous body of balloon material with a generally cylindrical shape when inflated in an elongated mold having a length corresponding to the desired length of said balloon and a generally square cross section with four side walls of substantially the same width connected by four corners, said elongated mold further having end members at each end, each of said end members having a pyramidal shape terminating in an apex with the corners of said mold corresponding with the corners of the end members;

heating said mold to the softening point of the balloon and forcing a pressurizing fluid into said balloon to urge said balloon material against the sidewalls and into said corners and into said end members whereby to establish stressed areas where said balloon engages said corners thereby forming four radially arranged ribs with webs therebetween, said ribs extending continuously from the distal to the proximal ends of said balloon, said webs being less stressed than said ribs due to greater expansion distances of said balloon material into said corners then to said sidewalls of said mold, said ribs and said webs constituting said balloon and being expandable from a folded condition for insertion into said body conduit to an expanded condition with a diameter substantially greater than its folded condition whereby to provide medical treatment to said conduit and thence, after treatment, into a folded condition with the webs collapsing inwardly towards said axis, said ribs extending parallel to said axis, each of said ribs being radially offset from adjacent ribs by substantially the same distance, whereby to form a balloon with ribs and webs as the body of the balloon, said balloon being expandable to a generally cylindrical shape by the introduction of an expansion fluid and thence collapsible upon the withdrawal of said fluid into a structure wherein said webs collapse towards said axis to enable easy withdrawal from said body conduit;

removing said balloon from said mold.

14. The balloon according to claim 13 wherein the balloon is heated in the mold to a temperature between about 160° and 195° C. and inflated at pressures between about 140 and 200 psi.

15. The catheter according to claim 13 wherein the balloon is formed of polyethylene terephthalate.

16. The catheter according to claim 13 wherein the balloon is formed of a base layer of polyethylene terephthalate with a layer of Selar disposed on either side of said base layer.

17. An inflatable medical balloon for subsequent attachment to a catheter shaft having a lumen for the introduction of an inflation fluid and subsequent introduction into a body conduit, said balloon being deflatable into a predetermined shape of minimal dimensions to be withdrawn from said body conduit, said balloon being formed by the steps comprising:

placing into an elongated mold an untensioned, preformed medical balloon, said balloon having continuous body of balloon material terminating in a tip and having a generally cylindrical shape when inflated, said mold having a length corresponding to the desired length of said balloon and a generally polygonal cross section with side walls of substantially the same width connected by corners, the spacing between opposed corners approximating the desired diameter of the balloon when inflated, said mold further having end members at each end, each of said end members having a pyramidal shape terminating in an apex, said corners of said mold corresponding with the corners of the end members and openings at the apexes to receive the catheter shaft and the tip of the balloon;

heating said mold to the softening point of the balloon and forcing a pressurizing fluid into said balloon to urge said balloon material against the sidewalls, into said corners and said into end members whereby to establish stressed areas where said balloon engages said corners thereby forming four radially arranged ribs with webs therebetween, said ribs extending continuously from the distal to the proximal ends of said balloon, said webs being less stressed than said ribs due to greater expansion distances of said balloon material into said corners than to said sidewalls of said mold, said ribs and said webs forming said balloon and being expandable from a folded condition for insertion into said body conduit to an expanded condition with a diameter substantially greater than its folded condition whereby to provide medical treatment to said conduit and thence, after treatment, into a folded condition with the webs collapsing inwardly towards said axis, said ribs extending parallel to said axis, each of said ribs being radially offset from adjacent ribs by substantially the same distance, whereby to form a balloon with ribs and webs as the body of the balloon, said balloon being expandable to a generally cylindrical shape by the introduction of an expansion fluid and then collapsible upon the withdrawal of said fluid into a structure wherein said webs collapse between said ribs towards said axis to enable easy withdrawal from said body conduit;

opening the mold and removing the balloon from said mold.

18. The balloon according to claim 17 wherein the balloon is heated in the mold to a temperature between about 160° and 195° C. and inflated at pressures between about 140 and 200 psi.

19. The balloon according to claim 17 wherein the balloon is formed of polyethylene terephthalate.

20. The balloon according to claim 17 wherein the balloon is formed of a base layer of polyethylene terephthalate with a layer of Selar polymer disposed on at least one side of said base layer.

* * * * *